United States Patent [19]

Fink et al.

[11] 4,360,731
[45] Nov. 23, 1982

[54] X-RAY DIAGNOSTIC INSTALLATION

[75] Inventors: Manfred Fink; Joerg Haendle, both of Erlangen, Fed. Rep. of Germany

[73] Assignee: Siemens Aktiengesellschaft, Berlin & Munich, Fed. Rep. of Germany

[21] Appl. No.: 227,943

[22] Filed: Jan. 23, 1981

[30] Foreign Application Priority Data

Feb. 22, 1980 [DE] Fed. Rep. of Germany ....... 3006774

[51] Int. Cl.³ .............................................. H04N 7/18
[52] U.S. Cl. ...................................... 378/42; 378/62; 378/99
[58] Field of Search ................ 250/416 TV, 322, 408, 250/413; 358/111

[56] References Cited

U.S. PATENT DOCUMENTS 3,126,480  3/1964  Bouwers ............................. 250/322

FOREIGN PATENT DOCUMENTS 2010360  9/1971  Fed. Rep. of Germany .. 250/416 TV
2032780  5/1978  Fed. Rep. of Germany .

Primary Examiner—Alfred E. Smith
Assistant Examiner—T. N. Grigsby

Attorney, Agent, or Firm—Hill, Van Santen, Steadman, Chiara & Simpson

[57] ABSTRACT

In an exemplary embodiment, radiography and fluoroscopy is carried out by a film cassette, an image intensifier television chain and a circuit for the automatic influencing of parameters determining the x-ray image quality, which circuit exhibits a radiation sensor, and a comparator for the comparison of a nominal setpoint value with the actual value delivered by the sensor, in which analog to digital converters are provided for the formation of an electric signal corresponding to the electrode voltages of the x-ray image intensifier, which electric signal is supplied in the form of an address to a memory in which the dependency of the conversion factor of the x-ray image intensifier upon the electrode voltage is stored. In addition, a converter is provided for the formation of an electric signal which is dependent upon the aperture of the x-ray collimator, which electric signal forms the address for a memory in which the dependency of the background of the x-ray image intensifier upon the aperture of the collimator determining the image format is stored. The output signals of the two memories are superimposed in an adder on the nominal setpoint value for the control loop.

7 Claims, 1 Drawing Figure

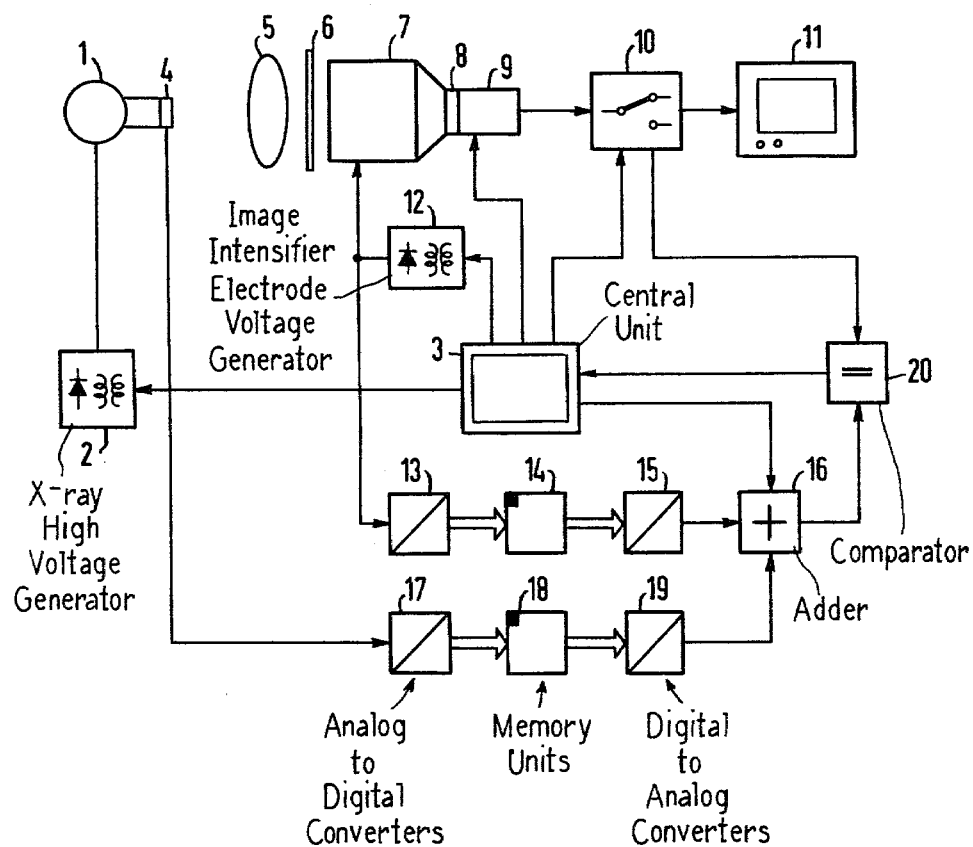

X-RAY DIAGNOSTIC INSTALLATION

BACKGROUND OF THE INVENTION

The invention relates to an x-ray diagnostic installation for radiography and fluoroscopy, comprising an image intensifier-television chain and a circuit for the automatic influencing of at least one parameter determining the x-ray image quality, which circuit exhibits a radiation sensitive sensor, a setpoint value transmitter and a comparator for the comparison of an adjusted setpoint value with the actual value delivered by the sensor.

X-ray diagnostic installations of this type are known in which the circuit is a control loop for the dose rate for the purpose of maintaining the mean image (or picture) brightness or dose at a selected value during a given exposure time. In addition, the circuit can also be a disconnect circuit which effects the switching-off of the x-ray tube upon attainment of a specific radiation dose. As sensors, photomultipliers or ionometric measuring chambers for the measurement of the dose rate behind the patient are employed. In addition, the image pickup tube may also be employed as sensor (German Pat. No. 20 32 780). The obtained signal current is either employed in order to interrupt the x-radiation upon attainment of an adjusted, desired dose setpoint value, which effects a sufficient film density in the case of a picture record (image exposure) or to influence the radiation dose rate, by means of corresponding control of the electric values at the x-ray tube, and determining said radiation dose rate, in such a manner that, in the case of fluoroscopy, the mean image brightness remains constant, or, in the case of expiration of a fixed photographic exposure time, the desired dose per image is obtained.

In the case of exposure of x-ray films with an automatic exposure timer several difficulties arise. In the case of x-ray film photographs with large area film formats in front of the x-ray image intensifier, only an ionization chamber arranged in front of the image cassette supplies a correct exposure. However, due to the arrangement of this measuring chamber in front of the x-ray image intensifier, the distance between the radiation image plane and the radiography subject is increased. The enlargement scale is thereby raised, as a consequence of which blurring (or unsharpness) in the radiation image is undesirably increased.

Therefore, for the purpose of light brightness control of the fluoroscopy image, a photomultiplier is employed which is subjected to the light which is coupled out of the path of rays of the optical (or lens) system between the x-ray image intensifier and the television camera, or the television camera is employed as sensor. The dependency of the x-ray image intensifier upon the size of the image format here influences the control adjustment, so that defective images can result.

The contrast transfer factor, i.e. the conversion factor of the x-ray image intensifier, is dependent inter alia upon the electrode voltage determining the image format. In addition, the background of the x-ray image intensifier influences the measurement. With increasing size of the image format defined by the collimator on the inlet fluorescent screen, the luminescence per unit area also increases. As a consequence of this, upon altering the image format, the luminescence at the outlet screen of the x-ray image intensifier can vary to such an extent that likewise defective images can result.

SUMMARY OF THE INVENTION

The invention proceeds from the object of producing a generic-type x-ray diagnostic installation whose image quality is independent of the image format selected by the collimator or the reproduction scale.

In accordance with the invention the object is achieved in that means for the formation of electrical signals corresponding to the image format are provided which are supplied in the form of addresses to storage means in which the dependency of parameters of the x-ray image intensifier upon the image format is stored, and that the output signal of the storage means generated by the respective address is superimposed in an adder on the nominal setpoint value for the circuit. The measured values undesirably falsified by the x-ray image intensifier are hereby corrected.

The influencing of the measured values by the conversion factor of the x-ray image intensifier can be corrected if control means generates an electric signal corresponding to the electrode voltages of the x-ray image intensifier, which electric signal is supplied in the form of an address to a memory in which the dependency of the conversion factor of the x-ray image intensifier upon the electrode voltage is stored. The influence of the background of the x-ray image intensifier can be eliminated if the control means generates an electric signal which forms the address for a memory in which the dependency of the background of the x-ray image intensifier upon the aperture of the collimator determining the image format is stored.

On the basis of an exemplary embodiment, the invention shall be explained in greater detail in the following having reference to the accompanying drawing sheet; and other objects, features and advantages will be apparent from this detailed disclosure and from the appended claims.

BRIEF DESCRIPTION OF THE DRAWINGS

The single FIGURE is a diagrammatic view showing an x-ray diagnostic installation in accordance with the present invention.

DETAILED DESCRIPTION

In the single FIGURE an x-ray tube 1 is illustrated which is energized by an x-ray high voltage generator 2 which is controlled by a central unit 3. Positioned in front of the radiation exit aperture of the x-ray tube is a collimator 4 which determines the radiation emergence (or exit) angle. A radiography subject 5 is located in the path of rays. An x-ray film cassette 6 is arranged behind the radiography subject 5. Following therebehind in the path of rays is an x-ray image intensifier 7 which forms a unit with an optical device 8 and a television camera 9. A monitor 11 is connected to the television camera 9 via a switchover installation 10.

The central unit 3 controls an electrode voltage generator 12 which generates the electrode voltage for the x-ray image intensifier 7. This voltage is supplied to an analog-to-digital converter 13 whose digital output signal forms the address for a memory 14; for example, a programmable read only memory (PROM). In this memory 14 the dependency of the x-ray image intensifier 7 upon the electrode voltage is stored. The digital output signal of the memory 14 is supplied to a D/A converter 15 whose analog output signal is connected to an adder 16.

From the collimator 4, via transmitters (position transducers), a voltage is obtained which indicates the size of the aperture of the collimator 4 and said voltage is supplied to an A/D converter 17 whose digital output signal corresponds to a memory location in a memory 18; for example, a PROM; i.e. which digital output signal forms the address for the memory 18. In this memory 18 the dependency of the background of the x-ray image intensifier 7 upon the aperture of the collimator 4 determining the image format is stored. The digital output signal of the memory 18 is supplied to a D/A converter 19 whose analog output is connected to the adder 16.

The two correction signals are superimposed in the adder 16 on a nominal setpoint value delivered by the central unit 3 and selected thereby by non-illustrated means. The output signal of the adder 16; i.e., the corrected setpoint value, is supplied to a comparator 20. This corrected setpoint value for the dose rate is compared in the comparator 20 with an actual value delivered by the television camera 9 for the purpose of maintaining the mean image brightness at a selected fixed value. An error signal is supplied to the central unit 3 from the output of the comparator 20, with which error signal the voltage of the x-ray generator 2 can be adjusted with the object of achieving an equilization of the actual value with the setpoint value.

The central unit 3 also assumes e.g. the control of the television camera 9, described in the German Pat. No. 2,032,780, for the formation of a signal corresponding to the radiation dose in the case of radiography. For this purpose, the central unit 3 interrupts the scanning beam operation of the television installation, connects the cathode of the image pickup tube to a potential for measuring the desired radiation dose of the radiographs, measures the radiation dose in a selected specified image section, and, via the switchover installation 10, connects the signal current to be measured to the comparator 20. In the case of radiography, upon attainment of a predetermined dose, the central unit 3 disconnects the x-ray tube 1.

Instead of the television camera 9, also a photomultiplier can be employed as the light-sensitive sensor for holding constant the mean image brightness, which photomultiplier would be connected to the optical device 8 in which, by means of a semi-transmissive mirror, at least one portion of the rays is coupled out onto the photomultiplier. The control of the television camera 9 by the central unit 3, as well as the switch-over installation 10, can, of course, be dispensed with here.

Through the described arrangement it has been possible to reduce the image blurring (or unsharpness) by virtue of the fact that the film camera can be moved close to the radiography subject. Through the utilization of the television camera as a sensor it has been possible to dispense with the ionometric measuring chamber, so that the construction is considerably simplified. The described arrangement is also suitable for control of the dose rate in the case of radiography with a fixedly prescribed photographic exposure time.

It will be apparent that many modifications and variations may be effected without departing from the scope of the novel concepts and teachings of the present invention.

We claim as our invention:

1. An x-ray diagnostic installation for radiography and fluoroscopy, comprising an image intensifier television chain including an x-ray image intensifier (7), and a control circuit for the automatic influencing of at least one parameter determining the x-ray image quality, said control circuit comprising a radiation sensitive sensor, a nominal value transmitter, and a comparator for the comparison of an adjusted setpoint value with an actual value generated by the sensor, the improvement comprising format responsive means (13, 17) for the formation of electric signals corresponding to the image format, memory means (14, 18) coupled with said format responsive means and being responsive to the value of electric signals therefrom to supply an output signal in accordance with the dependency of parameters of the x-ray image intensifier (7) upon the image format, and said control circuit including adder means (16) coupled with said memory means (14, 18) for receiving the output signal therefrom and for superimposing the same on the signal from the nominal value transmitter, thereby to adjust the setpoint value supplied to said comparator in accordance with the image format.

2. An x-ray diagnostic installation according to claim 1, with said format responsive means (13) being responsive to a signal in accordance with the magnitude of an electrode voltage of the x-ray image intensifier (7) to supply an electric signal which corresponds to an address of said memory means (14) such that said memory means (14) supplies an output signal according to the effective conversion factor of the x-ray image intensifier (7) with said electrode voltage applied thereto.

3. An x-ray diagnostic installation according to claim 1, with said installation including a collimator (4) with an adjustable aperture, said format responsive means (17) being responsive to a signal which is a function of the aperture of the collimator (4) to supply an electric signal which corresponds to an address of said memory means (18) such that said memory means (18) supplies an output signal according to the effective background of the x-ray image intensifier (7) for the selected aperture of the collimator (4).

4. An x-ray diagnostic installation according to claim 1, with said format responsive means (13, 17) comprising an analog to digital converter for the purpose of digitalization of the electrical signals supplied thereto, the memory means (14, 18) being responsive to digital signals in accordance with the output from said analog to digital converter to supply a digital output signal, and digital to analog converters (15, 19) connected at the output side of said memory means (14, 18) for supplying analog output signals to the adder means (16).

5. An x-ray diagnostic installation according to claim 1, with the radiation sensitive sensor comprising a television camera (9).

6. An x-ray diagnostic installation according to claim 1, with said control circuit comprising a control loop (3, 16, 20) for controlling the dose rate.

7. An x-ray diagnostic installation according to claim 1, with said control circuit comprising a switching circuit (3, 16, 20) for the purpose of switching-off of the x-radiation upon attainment of a predetermined radiation dose during radiographic operation.

* * * * *